United States Patent
Elkins (10) Patent No.: US 7,198,093 B1
(45) Date of Patent: *Apr. 3, 2007

(54) COMPLIANT HEAT EXCHANGE PANEL

(75) Inventor: William Elkins, San Jose, CA (US)

(73) Assignee: CoolSystems, Inc., Berkeley, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/127,256

(22) Filed: Jul. 31, 1998

(51) Int. Cl.
*F28F 3/12* (2006.01)
*A61F 7/08* (2006.01)

(52) U.S. Cl. .................. 165/46; 165/170; 29/890.039; 607/104; 607/108

(58) Field of Classification Search .................. 165/46, 165/170; 29/890.39; 607/104, 108–111, 607/114
See application file for complete search history.

(56) References Cited

U.S. PATENT DOCUMENTS

| | | | |
|---|---|---|---|
| 1,958,899 A * | 5/1934 | MacAdams | 165/170 X |
| 3,261,042 A | 7/1966 | Baker | |
| 3,320,682 A | 5/1967 | Sliman | |
| 3,738,367 A | 6/1973 | Hardy | |
| 3,830,676 A | 8/1974 | Elkins | |
| 4,147,921 A | 4/1979 | Walter et al. | |
| 4,149,541 A | 4/1979 | Gammons et al. | 128/400 |
| 4,471,759 A * | 9/1984 | Anderson et al. | 165/46 X |
| 4,597,384 A * | 7/1986 | Whitney | 601/152 |
| 4,678,027 A * | 7/1987 | Shirey et al. | 165/170 X |
| 4,691,762 A | 9/1987 | Elkins et al. | |
| 4,738,119 A | 4/1988 | Zafred | |
| 4,884,304 A | 12/1989 | Elkins | |
| 4,955,435 A | 9/1990 | Shuster et al. | 165/170 |
| 5,002,270 A | 3/1991 | Shine | |
| 5,014,695 A * | 5/1991 | Benak et al. | 165/46 |
| 5,033,136 A | 7/1991 | Elkins | |
| 5,080,166 A * | 1/1992 | Haugeneder | 165/46 |
| 5,086,771 A | 2/1992 | Molloy | 128/400 |
| 5,163,425 A | 11/1992 | Nambu et al. | |
| 5,241,951 A | 9/1993 | Mason et al. | 607/104 |
| 5,353,605 A | 10/1994 | Naaman | |
| 5,417,720 A | 5/1995 | Mason | 607/104 |
| 5,564,124 A | 10/1996 | Elsherif et al. | |
| 5,792,216 A | 8/1998 | Kappel | |
| 5,913,885 A | 6/1999 | Klatz et al. | |
| 5,967,225 A | 10/1999 | Jenkins | |
| 5,970,519 A | 10/1999 | Weber | |
| 6,030,412 A | 2/2000 | Klatz et al. | 607/104 |
| 6,117,164 A | 9/2000 | Gildersleeve et al. | 607/108 |
| 6,178,562 B1 * | 1/2001 | Elkins | 607/108 |
| 6,551,347 B1 | 4/2003 | Elkins | 607/104 |
| 6,695,872 B2 | 2/2004 | Elkins | |

FOREIGN PATENT DOCUMENTS

| | | | | |
|---|---|---|---|---|
| FR | 819022 | * | 10/1937 | 165/170 |
| IT | 330552 | * | 10/1935 | 165/46 |

* cited by examiner

*Primary Examiner*—Leonard R. Leo
(74) *Attorney, Agent, or Firm*—Reed Smith, LLP (57) ABSTRACT

A heat exchange panel for use in an active heat exchange system. The heat exchange panel includes first and second layers having seals between the layers at a common border, at fences, and at dots of a dot matrix. The dot matrix is organized into first parallel lines and second parallel lines where the first and second parallel line cross at a 90° angle. The seals at the border and the fences are rippled with smooth ripples.

7 Claims, 6 Drawing Sheets

COMPLIANT HEAT EXCHANGE PANEL

BACKGROUND OF THE INVENTION

1. Field of the Invention

The invention relates generally to heat exchangers and more particularly to a thin flexible heat exchange panel for transferring heat to or from a complex shape such as a portion of a human body.

2. Description of the Prior Art

Compliant heat exchange panels are used for cooling a portion of a human body for physical therapy, pre-game day conditioning, minor injury care, post orthoscopic surgery recovery, and as a replacement for general air-conditioning. The heat exchange panels operate by transferring heat from the human body to a heat absorbing medium having a lower temperature than the body. The heat exchange panel may be passive where the medium is stationary within the panel or active where the medium, typically a liquid, flows through the panel. A common example of a passive heat exchange panel is an ice pack. A limitation of a passive heat exchange panel is that the panel or the medium must be changed when the temperature of the medium rises. An active heat exchange system is more expensive because an external apparatus is required to pump and re-cool the liquid. However, an active heat exchange system is preferable for many applications because it can operate continuously over a long period of time while maintaining a constant controllable temperature.

In order to achieve the best results in an active heat exchange panel, the flowing liquid at every point within the panel must have a nearly constant temperature and the panel must be flexible in order to conform to the various complex shapes of the human body for thermal contact. These requirements are easier to meet when the heat exchange panel is very thin.

Figure 1A:
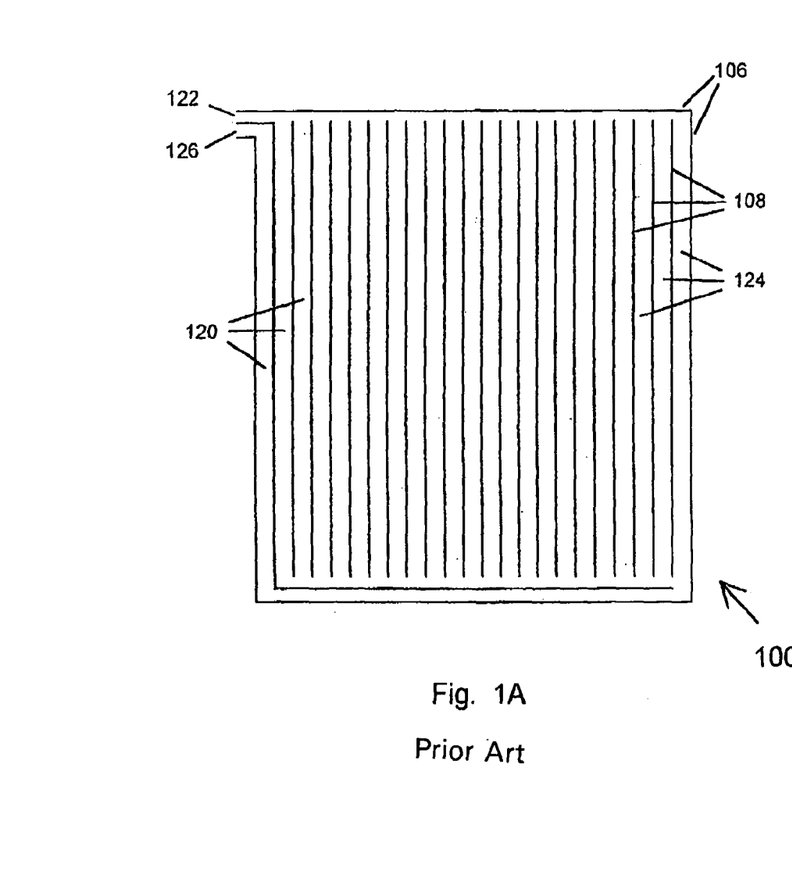
FIGS. 1A and 1B are plan and cross-sectional diagrams, respectively, of a first flexible heat exchange panel prior art.
Figure 1B:
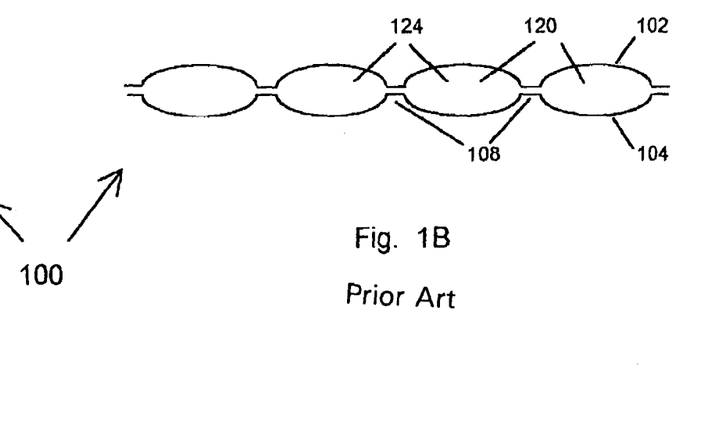

FIGS. 1A and 1B are cross-sectional and plan diagrams, respectively, of a heat exchange panel of the prior art referred to by a reference number 100 and disclosed by William Elkins in U.S. Pat. Nos. 4,884,304 and 5,033,136 for a "Bedding System With Selective Heating and Cooling". Similar heat exchange panels are disclosed by Elkins in U.S. Pat. Nos. 3,830,676 for a "Process of Making a Controlled Thermal Device" and U.S. Pat. No. 4,691,762 for a "Personal Temperature Control System". The heat exchange panel 100 includes a first layer 102 and a second layer 104. The first layer 102 and the second layer 104 are sealed together at a common border 106 and at fences 108. A liquid 120 is pumped so that it flows into an inlet port 122, through channels 124 between the fences 108, and out of an outlet port 126. The pressure of the liquid 120 causes the channels 124 to bulge to a certain thickness that depends upon the spacing of the fences 108. The panel 100 makes external thermal contact at the bulges over the channels 124. The fences 108 should be spaced as close together as possible in order for the panel 100 to be as thin as possible. However, spacing the fences 108 closer together requires an increase in the number of fences 108 and thereby reduces the area of the channels 124 where the panel 100 can make thermal contact.

In the heat exchange panel 100, the border 106 and the fences 108 are straight and essentially without wrinkles or ripples. Unfortunately, the straight border 106 and fences 108 cause the panel 100 to buckle when it is expanded with the liquid 120. The buckling impedes the flow of the liquid 120 and prevents the panel 100 from conforming closely to complex shapes. Elastic material could be used to alleviate these problems, however, the dimensions of elastic materials are more difficult to control.

Figure 2A:
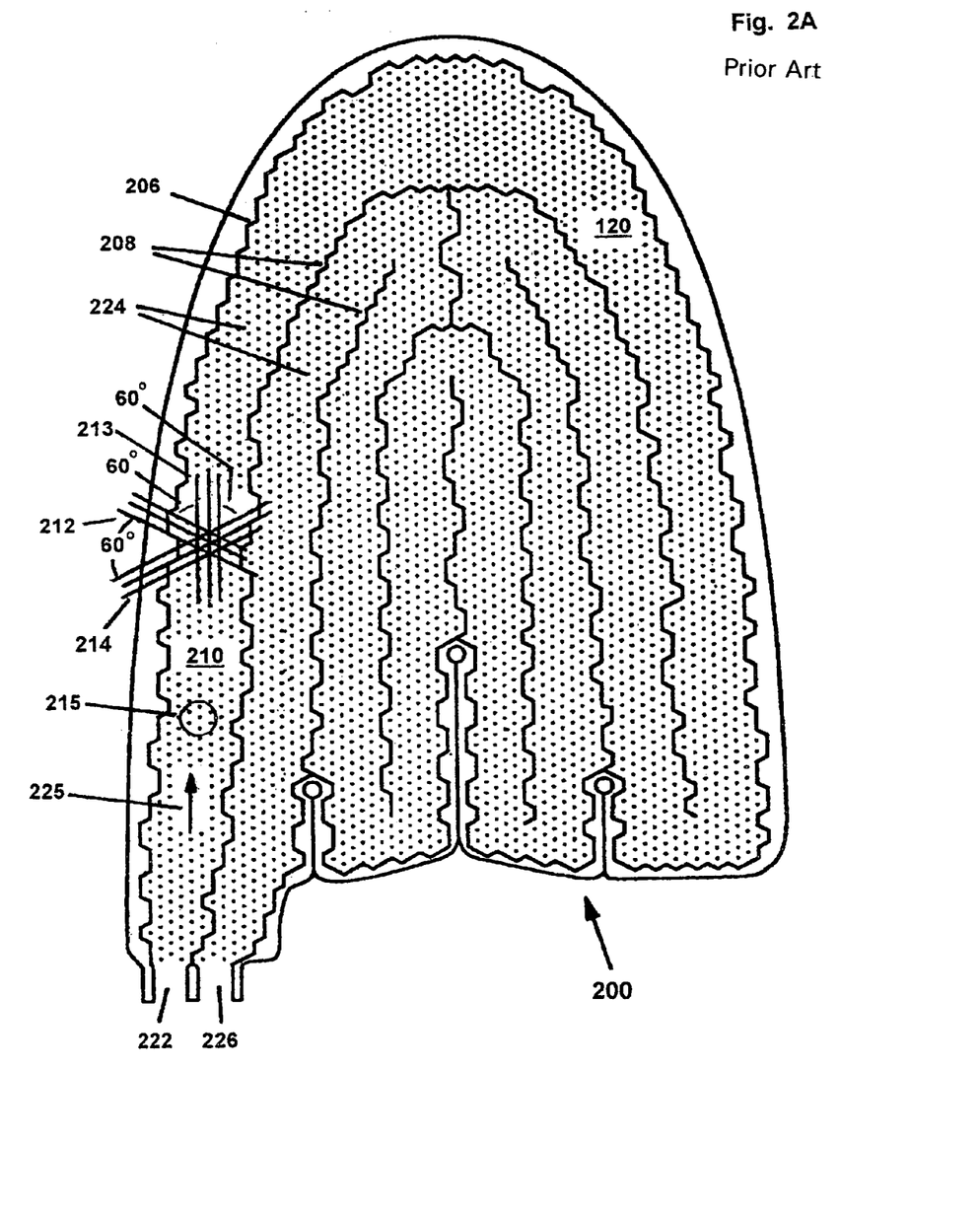
FIG. 2A is a plan diagram of a second flexible heat exchange panel of the prior art.
Figure 2B:
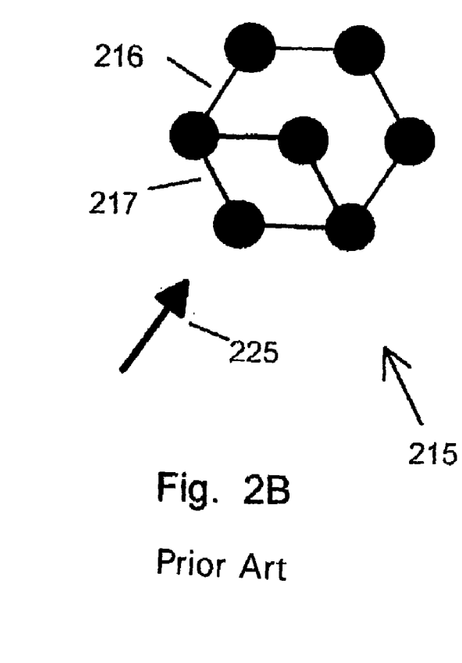
FIG. 2B is an expanded sect in of the plan diagram of the heat exchange panel of FIG. 2B.

FIG. 2A is a plan diagram of a heat exchange panel referred to by a reference number 200 that was developed in part to improve upon the heat exchange panel 100. The heat exchange panel 200 includes a first layer that is similar to the first layer 102 (FIG. 1A) and a second layer similar to the second layer 104 (FIG. 1A). The first layer and second layers of the panel 200 are sealed together at a common border 206, at fences 208, and at dots of a dot matrix 210. The dot matrix 210 is organized into first imaginary parallel lines L12, second parallel lines 213, and third parallel lines 214 for connecting each of the dots to the nearest adjacent dots of the dot matrix 210. The lines 212–14 cross each other at angles of approximately 60°. A typical section 215 of the panel 200 is expanded in FIG. 2B. The FIG. 2B shows each of the dots in the dot pattern. Each is at the center of an arc of six nearest adjacent dots. The six adjacent dots form a hexagonal pattern 216. Groups of four dots consisting of the center dot and a contiguous three of the nearest adjacent dots form a parallelogram 217. The liquid 120 is pumped to flow into an inlet port 222, between the fences 208, in a nominal direction 225 through the dot matrix 210, and out of an outlet port 226.

The pressure of the liquid 120 causes the channels 224 to bulge between the dots of the dot matrix 210 to a certain thickness that depends upon the spacing of the dots. The panel 200 makes external thermal contact at these bulges. The dots of the dot matrix 210 should be spaced as close together as possible in order for the panel 200 to be as thin as possible for conforming to complex shapes of various portions of the human body and avoiding warm spots due to relative stagnation of the liquid flow. However, increasing the number of dots of the dot matrix 210 reduces the area of the bulges where the panel 200 can make thermal contact. Consequently, it is important to space the dots of the dot matrix 210 as close together as possible while using a minimum number of dots. Unfortunately, while an improvement over the panel 100, the heat exchange panel 200 having the dot matrix 210 having the lines 212–14 crossing at angles of 600 with the hexagonal pattern 216 is not optimum in this respect.

The panel 200 differs from the panel 100 by having trapezoid and triangular shaped wrinkles in the border 206 and the fences 208. The wrinkles reduce the tendency to buckle when the panel 200 is inflated and enable the panel 200 to conform better to complex shapes as compared to the panel 100. However, the hard or, in other words, adrupt corners of the wrinkles decrease the laminar flow of the liquid 120 enabling thermal zones of warmer liquid to form, thereby reducing the performance of the heat exchange panel 200.

SUMMARY OF THE INVENTION

It is therefore an object of the present invention to provide a compliant heat exchange panel that is superior to the prior art for conforming and making thermal contact to complex shapes and for providing a more uniform temperature.

Briefly, in a preferred embodiment, the heat exchange panel of the present invention includes first and second layers which are conformable to complex shapes and have seals between the layers at a common border, at fences, and at dots of a dot matrix. The dot matrix is organized into first imaginary parallel lines and second imaginary parallel lines that connect each of the dots to the nearest adjacent dots at a 90° angle. In an active heat exchange panel, the first and second parallel lines are generally 45° to the direction of fluid flow. The seals at the border and the fences are rippled with no sharp changes in direction (curvilinear nipples).

An advantage of a heat exchange panel of the present invention is that a dot matrix attachment pattern is organized for providing a greater area of thermal contact by minimizing the number of dot attachments for a given panel thickness when inflated and maintaining a more constant panel thickness.

Another advantage of a heat exchange panel of the present invention is that border and fence seals are rippled thereby reducing buckling when the panel is inflated.

An advantage of an active heat exchange panel of the present invention is that a dot matrix pattern provides a more uniform temperature through better mixing of a fluid flow.

Another advantage of an active heat exchange panel of the present invention is that border and fence seals have smooth ripples i.e., ripples having no sharp changes in direction as stated above (curvilinear ripples) thereby providing greater compliance and reducing areas of stagnation for a more uniform temperature.

These and other objects and advantages of the present invention will no doubt become obvious to those of ordinary skill in the art after having read the following detailed description of the preferred embodiments which are illustrated in the various figures.

DETAILED DESCRIPTION OF THE PREFERRED EMBODIMENTS

Figure 3A:
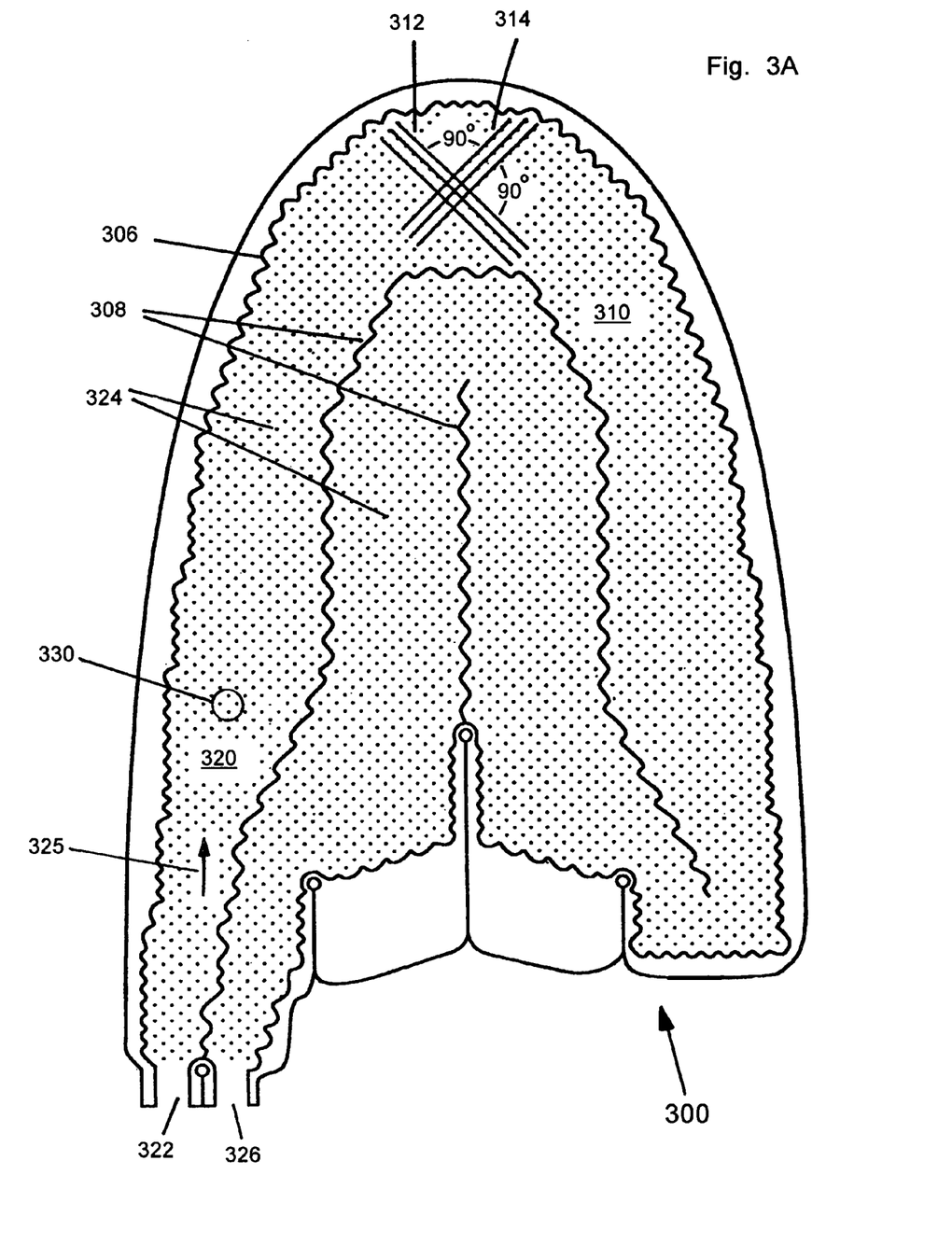
FIGS. 3A and 3B are plan and cross-sectional diagrams, respectively, of a flexible heat exchange panel of the present invention.
Figure 3B:
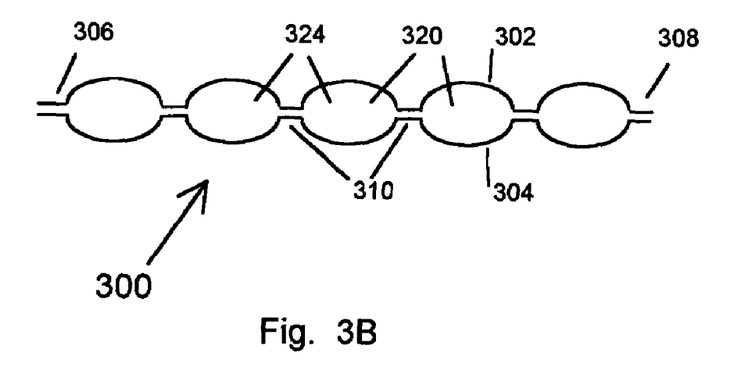

FIGS. 3A and 3B are a plan and a cross-sectional diagram, respectively, of a heat exchange panel of the present invention and referred to by a reference number 300. The heat exchange panel 300 includes a first layer 302 and a second layer 304. The first layer 302 and the second layer 304, which layers are conformable to complex shapes are sealed together at a common border 306, at fences 308, and at dots of a dot matrix 310. Preferably, the common border 306 is near to the perimeters of the first layer 302 and the second layer 304 but it does not need to be at the exact outside of the first layer 302 or the second layer 304. The dot matrix 310 is organized into first imaginary parallel lines 312 and second imaginary parallel lines 314 for connecting each of the dots to the nearest adjacent dots of the dot matrix 310. The lines 312 and 314 are approximately perpendicular within a range ±20°. In contrast, in the prior art panel 200 (FIGS. 2A–B) the lines 212–14 cross at angles of about 60°, thereby requiring a greater number of dots in the dot matrix 210 (FIGS. 2A–B) and reducing the area of thermal contact unless the panel 200 is allowed to be thicker.

Figure 3C:
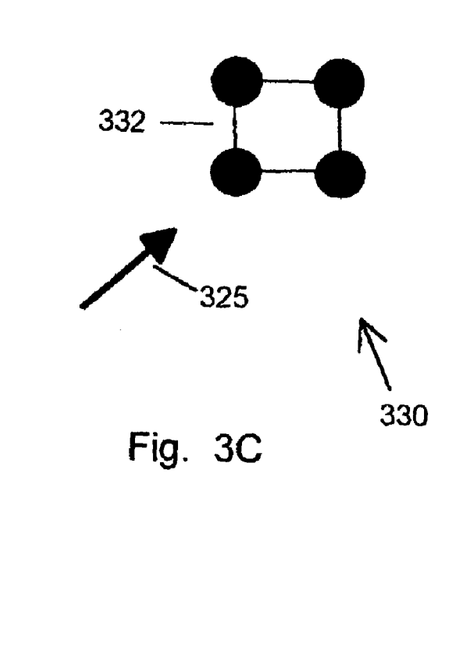
FIG. 3C is an expanded section of the plan diagram of the heat exchange panel of FIGS. 3A–B.

In a passive application, the panel 300 is filled with a gel, a liquid, or other flexible medium having a desired temperature for transferring heat to or from an external body. The panel 300 is then wrapped about an external body in a manner to make the greatest area of thermal contact in order to transfer heat between the body and the medium. Typically, the panel 300 is used for cooling a limb, torso, neck, or head of a human being. The medium is replaced when its temperature increases or decreases outside of a desirable range. However, preferably, the panel 300 is used in an active application where a fluid 320 is pumped to flow into an inlet port 322, between the fences 308, through channels 324 in a nominal direction 325 around and past the dots of the dot matrix 310, and out of an outlet port 326. As illustrated, inlet port 322 and outlet port 326 are contiguous. The movement of the fluid 320 around the dots of the dot matrix 310 causes a continuous mixing of the fluid 320. The mixing is important for avoiding warm spots and maintaining a uniform temperature. In order to promote such mixing, clear channels are avoided between the dots of the dot matrix 310 by arranging the first lines 312 and the second lines 314 at angles between 25° and 65°, preferably about 45°, with respect to the nominal direction 325 of flow of the fluid 320. FIG. 3C shows an expanded view of a typical section 330 of the panel 300. Each of the dots in the dot pattern is a corner of a square pattern 332.

The dots of the dot matrix 310 may be customized at the bends of the channels 324 to maintain an angle of approximately 45° of the lines 312 and 314 to the direction of the flow of the fluid 320 in the locality of the bends. In contrast, in the prior art panel 200 (FIGS. 2A–B) the second parallel lines 213 are generally arranged parallel to the nominal direction 225 (FIGS. 2A–B) of the flow of the liquid 210 resulting in clear channels where the liquid 210 can avoid mixing. The border 306 and the fences 308 are smoothly rippled with ripple cycle lengths that are substantially less than the lengths of the border 306 or the fences 308. In this connection, as can be seen from the drawing, the resulting smooth ripples are generally sinusoidal and have a repeating (cyclic) pattern. Such ripples further promote mixing of the fluid 320. The inlet port 322 and the outlet port 326 are preferred to have openings in the seal in the border 306 as shown in FIG. 3A. The ports 322 and 326 may be reversed, thereby reversing the nominal direction 325 of fluid flow. Alternatively, the inlet port 322 and/or the outlet port 326 may have openings in the first layer 302 or the second layer 304. Preferably, the fluid 320 is a liquid, however, a gas may be used. In a preferred embodiment, the dots of the dot matrix 310 have a diameter of about 0.100 inches and a center to center spacing of about 0.250 inches when the panel 300 is flat. When the panel 300 is filled with the medium or fluid, the channels 324 bulge to a height of about 0.060 to 0.080 inches high by about 0.100 to 0.120 inches wide. The first layer 302 and the second layer 304 are an impermeable laminate having a fabric, such as Nylon, and three layers of Ether-based Polyurethane. The first layer of Polyurethane applied to the fabric has a relatively low density, the second layer has a relatively high density, and the third layer has a relatively low density in the laminating process that is available from Highland Industries of Framingham, Mass. A Radio Frequency (RF) heat sealing process available from Ocean Vendors of Byron, Calif., is used for sealing the first layer 302 to the second layer 304 at the border 306, the fences 308, and the dots of the dot matrix 310 so that the fabric of the laminate is on the outside of the panel 300. Plates for the sealing process are made of Magnesium with a photo engraving process available from Custom Photo Engraving of Redwood City, Calif. Further information for the materials and processes for constructing the heat exchange panel 300 is disclosed by William Elkins in the U.S. Pat. Nos. 3,830,676, 4,691,762, 4,884,304, and 5,033,136 incorporated herein by reference.

Figure 4:
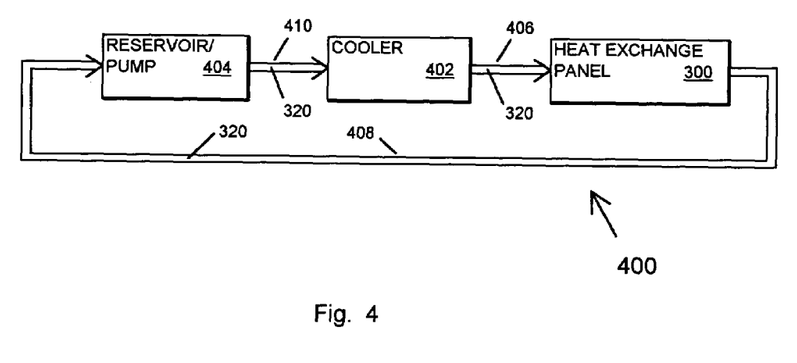
FIG. 4 is a block diagram of a system of the present invention using the heat exchange panel of FIGS. 3A–C.

FIG. 4 is a block diagram of a preferred embodiment of a system of the present invention and referred to by a reference number 400. The system 400 includes at least one heat exchange panel 300, the fluid 320, a heat transfer device such as a heater or a cooler 402 having a temperature control, a reservoir/pump 404, and conduits 406, 408, and 410. The cooler 402 cools the fluid 320 to a selected temperature and passes the cooled fluid 320 through the conduit 406 to the heat exchange panel 300. The cooled fluid 320 passes through the heat exchange panel 300 where it absorbs or passes heat energy through the first layer 302 and/or the second layer 304 from or to a human body or other external source of heat that is to be cooled or heated. From the heat exchange panel 300 the fluid 320 passes through the conduit 408 to the reservoir/pump 404. The reservoir/pump 404 stores a supply of the fluid and pumps the fluid 320 through the conduit 410 to the cooler 402 completing a fluid circuit.

Although the present invention has been described in terms of the presently preferred embodiments, it is to be understood that such disclosure is not to be interpreted as limiting. Various alterations and modifications will no doubt become apparent to those skilled in the art after having read the above disclosure. Accordingly, it is intended that the appended claims be interpreted as covering all alterations and modifications as fall within the true spirit and scope of the invention.

What is claimed is:

1. A heat exchange panel to be conformed to a complex shape, comprising:
    a first layer of a flexible material, which layer is conformable to a complex shape;
    a second layer of a flexible material, which layer also is conformable to a complex shape and has a common border with the first layer;
    a border seal sealing substantially an entire periphery of the first layer and the second layer at said border; and
    said first and second layers being directly secured together interiorly of said border at a multiplicity of points to from a dot matrix of attachments organized into first imaginary lines and second imaginary lines for connecting dots of said dot matrix to nearest dots of said dot matrix, said first imaginary lines crossing said second imaginary lines at an angle falling in a range of between about 70° to about 110°;
    wherein:
    the border seal consists of curvilinear ripples having ripple cycle lengths substantially shorter than the length of said border, forming an irregular border with respect to the dot matrix of attachments, in order to provide uniform flow and pressure, further comprising:
    a first port for passing fluid into the panel;
    a second port for passing said fluid out of the panel; and
    at least one fence interiorly of said border sealing the first layer and the second layer, said fence cooperating with said border to define a fluid flow channel within said panel, wherein:
    the fence includes curvilinear ripples having ripple cycle lengths substantially shorter than the length of the fence.

2. The panel of claim 1 wherein said first and second ports are contiguous.

3. A method of manufacturing a heat exchange panel which conforms to a complex shape comprising steps of:
    sealing a first layer of a flexible material, which layer is conformable to a complex shape to a second layer of a flexible material at a common border, which second layer is also conformable to a complex shape; and
    sealing said first layer to said second layer interiorly of said border at a multiplicity of points to form a dot matrix of attachments, said dot matrix organized into first imaginary lines and second imaginary lines for connecting dots of said dot matrix to nearest dots of said dot matrix, said first imaginary lines crossing said second imaginary lines at an angle falling in a range of between about 70° to about 100°;
    further comprising steps of:
    constructing first and second ports for passing a fluid into and out of said panel; and
    sealing said first layer to said second layer with at least one fence between said first port and said second port, said fence having curvilinear ripples having ripple cycle lengths substantially shorter than the length of said fence, forming an irregular border with respect to the dot matrix of attachments, in order to provide uniform flow and pressure.

4. A method for exchanging heat with a complex shape, comprising steps of:
    receiving a fluid flow in a first port;
    restricting passage of said fluid flow to between first and second layers of flexible material which are conformable to a complex shape;
    further restricting said passage with a border seal at a common border between said first and said second layers;
    passing said fluid flow about a multiplicity of points interiorly of said first and second layers, said first and second layers being directly secured together to form a dot matrix of attachments organized into first imaginary lines and second imaginary lines connecting dots of said dot matrix to nearest dots of said dot matrix, said first imaginary lines crossing said second imaginary lines at an angle falling in a range of between about 70° to about 110°; and
    issuing said fluid flow through a second port;
    further restricting said fluid flow with at least one fence between said first port and said second port;
    wherein:
    said fence includes curvilinear ripples having ripple cycle lengths substantially shorter than the length of the sealing fence, forming an irregular border with respect to the dot matrix of attachments, in order to provide uniform flow and pressure.

5. A system for exchanging heat with a complex shape, comprising:
    a heat transfer device for one of cooling or heating a fluid;
    a pump/reservoir coupled to the heat transfer device for storing and pumping said fluid; and
    a heat exchange panel coupled to the pump/reservoir and the heat transfer device, the heat exchange panel including a first layer of a flexible material conformable to a complex shape, a second layer of a flexible material also conformable to a complex shape, a border seal sealing said first layer and said second layer together at said border, a first port for receiving said fluid, a second port contiguous with said first port for issuing said fluid, and said first and second layers being directly secured together interiorly of said border seal to form a dot matrix of attachments between said first and second layers, said dot matrix organized into first imaginary lines and second imaginary lines for connecting dots of said dot matrix to nearest dots of said dot matrix, said first imaginary lines crossing said second imaginary lines at an angle falling in a range of between about 70° to about 110°;

wherein: the heat exchange panel further includes at least one fence interiorly of the border sealing said first layer and said second layer, said fence cooperating with said border to define a fluid flow channel within said panel; and wherein:

said fence includes curvilinear ripples having ripple cycle lengths substantially shorter than the length of said fence, forming an irregular border with respect to the dot matrix of attachments, in order to provide uniform flow and pressure.

6. A heat exchange panel to be conformed to a complex shape, comprising:

a first layer of a flexible material, which layer is conformable to a complex shape;

a second layer of a flexible material, which layer also is conformable to a complex shape;

a border seal sealing substantially an entire periphery of the first layer and the second layer to form a border, the border seal consisting of curvilinear ripples having ripple cycle lengths substantially shorter than the length of said border forming an irregular border with respect to the dot matrix of attachments, in order to provide uniform flow and pressure, further including at least one fence interiorly of said border, which fence is sealed to the first layer and the second layer and includes curvilinear ripples having ripple cycle lengths substantially shorter than the length of the fence forming an irregular border with respect to the dot matrix of attachments, in order to provide uniform flow and pressure.

7. The heat exchange panel of claim 6 further including a first port for passing fluid into the panel and a second port for passing said fluid out of the panel, said first and second ports being contiguous.

* * * * *